United States Patent [19]
Wang et al.

[11] Patent Number: 5,734,092
[45] Date of Patent: Mar. 31, 1998

[54] PLANAR PALLADIUM STRUCTURE

[75] Inventors: Tak K. Wang, Havertown, Pa.; James W. Baker, Elkton, Md.

[73] Assignee: Hewlett-Packard Company, Palo Alto, Calif.

[21] Appl. No.: 640,425

[22] Filed: Apr. 30, 1996

Related U.S. Application Data

[63] Continuation-in-part of Ser. No. 456,210, May 31, 1995.

[51] Int. Cl.$^6$ ..................................................... G01N 7/00
[52] U.S. Cl. .......................................... 73/23.25; 73/23.2
[58] Field of Search ................................ 73/23.2, 23.21, 73/23.22, 23.23, 23.24, 23.25, 23.26

[56] References Cited

U.S. PATENT DOCUMENTS

| | | | |
|---|---|---|---|
| 1,174,631 | 3/1916 | Snelling | 96/10 |
| 2,961,062 | 11/1960 | Hunter et al. | 183/2 |
| 3,246,764 | 4/1966 | McCormack | 210/321 |
| 3,665,680 | 5/1972 | Heuser | 55/158 |
| 3,718,434 | 2/1973 | Pierce | 23/232 R |
| 4,024,036 | 5/1977 | Nakamura et al. | 204/129 |
| 4,318,828 | 3/1982 | Chapman | 252/465 |
| 4,329,157 | 5/1982 | Dobo et al. | 55/16 |
| 4,364,759 | 12/1982 | Brooks et al. | 55/487 |
| 4,713,234 | 12/1987 | Weerich et al. | 423/648 R |
| 4,761,164 | 8/1988 | Pez et al. | 55/16 |
| 4,886,048 | 12/1989 | Labaton et al. | |
| 5,139,975 | 8/1992 | Herron et al. | 501/7 |
| 5,304,330 | 4/1994 | Tatarchuk et al. | 264/61 |
| 5,451,386 | 9/1995 | Collins et al. | 423/237 |
| 5,498,278 | 3/1996 | Edlund | 96/11 |
| 5,545,784 | 8/1996 | Weitkamp et al. | 585/250 |
| 5,569,633 | 10/1996 | Carolan et al. | 502/4 |

OTHER PUBLICATIONS

J.E. Lovelock, "Solute Switching And Detection By Synchronous Demodulation In Gas Chromatography," Journal Of Chromatography, 112 (1975), pp. 29–36.

J.R. Young, "Palladium–Diaphragm Hydrogen Pump," The Review of Scientific Instruments, vol. 34, No. 4, Apr. 1963, pp. 374–377.

J.E. Lovelock, P.G. Simmonds, and G.R. Shoemake, "The Palladium Generator–Separator–A Combined Electrolytic Source And Sink For Hydrogen In Closed Circuit Gas Chromatography," Analytical Chemistry, vol. 42, No. 9, Aug. 1970, pp. 969–973.

"Rare–Earth Filter Makes Pure Hydrogen," New Trends, Machine Design, Aug. 10, 1995, p. 18.

J.E. Lovelock, P.G. Simmonds, G.R. Shoemake, and S. Rich, "Palladium Devices For Gas Chromatography," Journal of Chromatographic Science, Aug., 1970, vol. 8, pp. 452–456.

Final Report: "Development of A Hydrogen Separator for The Separation of Dissolved Hydrogen in Fuel Cell Water," Apollo Applications Program 69–5358, Nov., 1969, prepared by C.F. Albright, N.E. Wood, pp. 1–1—4–12.

J.E. Lovelock, P.G. Simmonds, and G. R. Shoemake, Rare Gases of the Atmosphere: "Gas Chromatography Using A Termal Conductivity Detector And A Palladium Transmodulator," Analytical Chemistry, vol. 43, No. 14, Dec., 1971, pp. 1958–1961.

M.R. Stevens, C.E. Giffin, G.R. Shoemake, and P.G. Simmonds, "A Portable Self–Contained Gas Chromatograph," The Review Of Scientific Instruments, vol. 43, No. 10, Oct., 1972, pp. 1530–1534.

*Primary Examiner*—Hezron E. Williams
*Assistant Examiner*—Jay L. Politzer
*Attorney, Agent, or Firm*—Mark Z. Dudley

[57] ABSTRACT

A planar palladium structure makes use of the unique properties of palladium to provide a hydrogen permeable membrane suitable for use in providing, for example, selective control of a nominal gas pressure within a cavity. The contemplated planar palladium structure includes a planar substrate having upper and lower major surfaces and an array of microfine channels therebetween, wherein the channels allow gaseous communication between the upper and lower major surfaces, and an array of palladium deposits being distributed on the substrate and located with respect to the microfine channels so as to restrict the gaseous communication to diffusion of hydrogen gas.

11 Claims, 2 Drawing Sheets

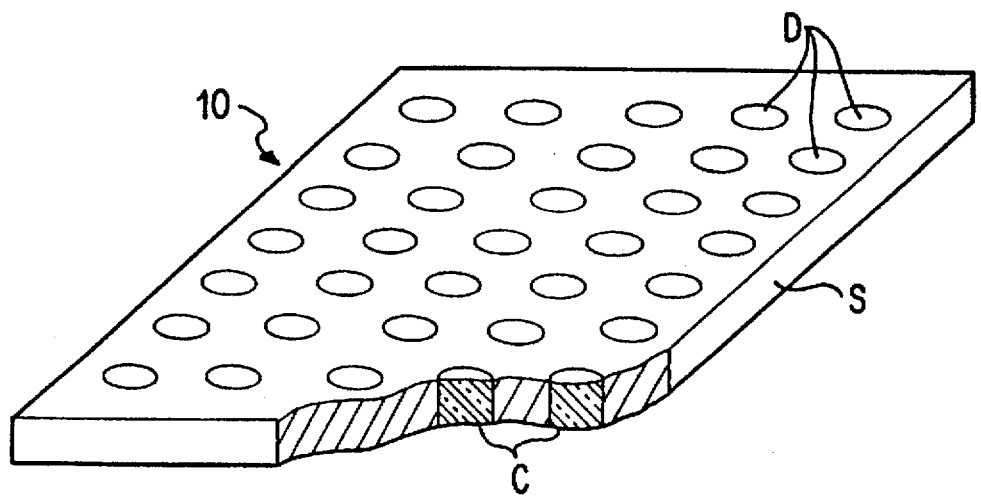
FIG. 1
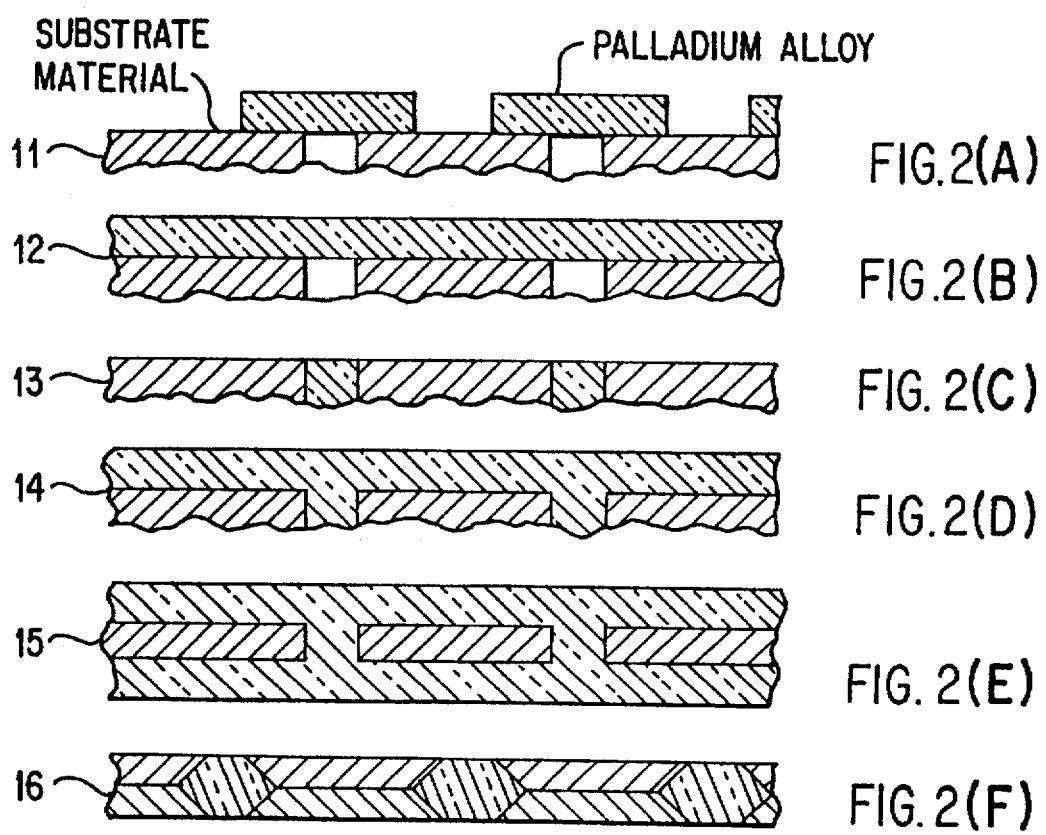
FIG. 2(A)
FIG. 2(B)
FIG. 2(C)
FIG. 2(D)
FIG. 2(E)
FIG. 2(F)

PLANAR PALLADIUM STRUCTURE

CROSS REFERENCE TO RELATED APPLICATION

This application is a continuation-in-part of commonly-assigned, copending U.S. patent application Ser. No. 08/456,210 filed May 31, 1995 entitled THERMAL ISOLATION SYSTEM IN AN ANALYTICAL INSTRUMENT and filed in the name of Tak Kui Wang, James W. Baker, and Terry A. Berger.

FIELD OF THE INVENTION

The present invention relates to methods and apparatus for the provision of a structure suitable for effecting controlled diffusion of hydrogen therethrough, and in particular to a planar palladium structure operable as a hydrogen-permeable membrane.

BACKGROUND OF THE INVENTION

A continuous structure formed of palladium, or of an alloy of palladium with certain metals, is known to operate as a membrane or filter that is permeable by hydrogen. The palladium is typically provided in the form of an alloy so as to provide a malleable material. For example, a heated palladium (Pd) or palladium-silver (Pd—Ag) diaphragm has been operated to evacuate hydrogen from a container (see, e.g., Young, J. R., "Palladium-Diaphragm Hydrogen Pump", *The Review of Scientific Instruments*, Volume 34, Number 4, April 1963). Other uses of palladium in a gas permeable membrane may be found in, for example: Lovelock, J. E., et. al., "Palladium Devices for Gas Chromatography", *Journal of Chromatographic Science*, Vol. 8, August 1970; "Stable Palladium Alloys for Diffusion of Hydrogen", *NASA Tech Brief* 73-10024 from JPL Invention Report DO-2385/NPO-11747, Buttler, W. P., California Institute of Technology, Pasadena, Calif., July 1973; Labaton, et. al., "Hydrogen Pump", U.S. Pat. No. 4,886,048.

The conventional hydrogen-permeable membrane is typically provided in a thin, continuous structure such as a hollow tube or sheet formed of palladium alloy, or as a thin, continuous layer of palladium alloy that is laminated on a supporting substrate that is also permeable to hydrogen. Hydrogen dissolved in palladium has been observed to cause the palladium to expand; a conventional palladium structure is therefore subject to stress forces and deformation that develop during cycles of expansion and contraction of the palladium. The resulting deformation and unrelieved mechanical stress causes warping, wrinkling, fracturing, or delamination of the membrane.

Accordingly, there is a need for a palladium structure operable as a hydrogen-permeable membrane that can withstand high concentrations of dissolved hydrogen without becoming subject to failure.

SUMMARY OF THE INVENTION

The present invention is directed to a novel planar palladium structure suitable for use as a hydrogen-permeable membrane. The contemplated planar palladium structure makes use of the unique properties of palladium or a palladium alloy to allow selective control of a flow of hydrogen through deposits of palladium distributed with respect to channels within a supporting substrate so as to make the channels permeable only by hydrogen. The substrate thereby constrains the deformation of the palladium deposits due to the presence therein of dissolved hydrogen, thus minimizing or preventing the failure modes experienced in the prior art.

In a first embodiment of the invention, the planar palladium structure is provided in the form of a perforated or porous planar substrate having first and second major surfaces, an array of channels each of which extend between the first and second major surfaces, and an array of discrete, thin-film deposits of palladium distributed on the planar substrate so as to make the channels permeable only by hydrogen. The bulk of the substrate that defines the channels is preferably formed of a material that prevents gas flow between the first and second major surfaces. The substrate material need not be permeable to hydrogen. The planar palladium structure may thus be configured as a hydrogen-permeable membrane.

In a first preferred embodiment on the invention, an array of thin-film, discrete palladium deposits are integrated with the substrate such that the deposits substantially fill the full depth of the channels in the substrate. Alternatively, the palladium may be provided in the form of plural thin-film deposits such that the deposits occupy only a portion of the depth of the channels. In another alternative embodiment, a thin-film layer of palladium may overlie the channel opening at one of the major surfaces.

The substrate provides mechanical strength and rigidity to the planar structure, while channels and palladium deposits act as a hydrogen-selective diffusion path between the first and second major surfaces.

In a first aspect of the invention, the provision of palladium in the form of deposits within respective channels allows the bulk of the substrate to constrain the expansion and contraction of the palladium deposits during hydrogen diffusion. As a result, the expansion and contraction experienced by the palladium deposits causes no significant damage to the deposits or substrate. The planar palladium structure may thus be used to provide a hydrogen-permeable membrane that is operable even at high rates of hydrogen diffusion without the failure modes observable in prior art palladium structures.

In another aspect of the invention, the provision of palladium in the form of deposits within respective channels allows the bulk of the substrate to act as a mechanical support for the palladium deposits. As a result, the palladium deposits may be provided in thicknesses that correspond to a thin-film layer. Because the planar palladium structure may be constructed to have a large surface area having a multiplicity of gas-permeable channels, the preferred embodiments of the structure can diffuse hydrogen more efficiently than demonstrated by conventional palladium structures.

In another aspect of the invention, the substrate may include channels that take the form of regularly spaced microfine channels and thus distribution of the palladium deposits on the substrate forms what is considered a cellular array of palladium deposits.

In another aspect of the invention, the substrate may include channels that take the form of irregularly spaced microfine channels in a porous substrate.

In another aspect of the invention, the planar palladium structure may include heating means for heating the palladium deposits and thereby enhancing the diffusion of hydrogen through the palladium deposits.

In another preferred embodiment of the invention, a hydrogen pump system may be constructed according to the present invention to include a housing that defines a closed cavity, a planar palladium structure attached within the closed cavity so as to provide upper and lower subcavities, means for heating or cooling the planar palladium structure, and a system for providing hydrogen in at least one of the upper and lower subcavities.

The advantages of the present invention include the ability to construct a hydrogen-permeable membrane in a planar structure having a very large surface area. Such a large surface area enhances the ability of the membrane to diffuse hydrogen at an elevated rate. Further, the contemplated membrane may be operated at high concentrations of hydrogen dissolved in the palladium deposits without experiencing the degree of structural deformation and failure that is exhibited by conventional membranes.

BRIEF DESCRIPTION OF THE DRAWINGS

FIG. 1 is simplified side perspective view of a preferred embodiment of a planar palladium structure constructed according to the present invention, with a portion of the planar palladium structure illustrated in cross-section.

FIGS. 2 and 3 are simplified side cross-sectional representations of preferred embodiments of the planar palladium structure constructed according to the present invention.

DETAILED DESCRIPTION OF THE PREFERRED EMBODIMENTS

For the purposes of description of the present invention, "palladium deposits" will be understood to describe thin-film deposits of either pure palladium or palladium alloy; "planar structure" will be understood to include both flat, folded, and curved planar structures; a "planar substrate" is meant to include a supporting structure having opposed upper and lower major surfaces; "channels" will be understood to include passageways having distal ends located at the upper and lower major surfaces of the planar substrate, and as such may be understood to include small vias (e.g., passages between layers), porous or tortuous channels, honeycomb structures, bores, and the like; and "microfine channels" will be understood to describe closely-adjacent, substantially parallel channels each having an average diameter in the range of about 0.1 to 2 micrometers. The distribution of palladium deposits "in" a channel is meant to describe a deposit so located as to make the respective channel permeable only by hydrogen gas. Such distribution contemplates the deposit being fully contained by the channel, as well as a deposit that forms a barrier layer over an opening at one of the channel ends. The average thickness of the contemplated substrate is contemplated as being provided in the range of 0.1 micrometers to 2 millimeters; the palladium deposits are contemplated as having an average thickness in the range of 0.1 micrometers to 1 millimeter.

FIGS. 1, 2A–2F, and 3 illustrate exemplary planar palladium structures 10–17 constructed according to the present invention. Each of the illustrated planar structures includes a plurality of thin-film palladium deposits D located in or about fine channels C in a planar substrate S. The palladium deposits are preferably deposited as a thin film using known techniques such as physical vapor deposition (PVD), screen printing, sputtering, or electron-beam evaporation and receive surface treatment to enhance hydrogen pumping efficiency. As particularly illustrated in FIGS. 2B and 2E, bonding of a thin foil of palladium to the substrate S is another method contemplated for application of the palladium. Each of the preferred planar structures 10–16 thus comprises an array of palladium alloy cells, each of which is permeable only by hydrogen gas. One preferred substrate S having regularly-spaced microfine channels C may be obtained as a microchannel plate from Galileo Electro-Optics, W. Sturbridge, Mass.

Figure 3:
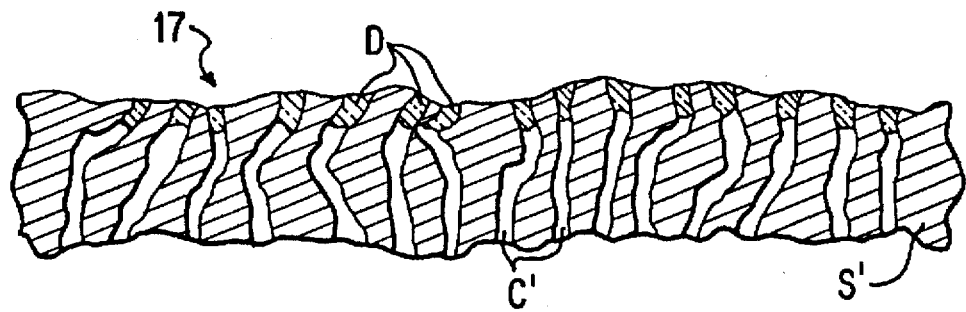

While the palladium deposits D are shown to be located in an array of evenly-spaced channels C, the channels need not be so regularly distributed in the substrate. As shown in FIG. 3, the substrate S' may be composed of a porous structure and thereby include a microfine array of tortuous channels C'. In such an embodiment, the palladium deposits D would be distributed such that each deposit D overlies or fills at least a portion of a respective channel C'.

Silver, gold, and nickel are preferred metals for use in preparing a palladium alloy suitable for the composition of the deposits D.

The preferred compositions of the substrates S, S' include alumina, glass, ceramics, and silicon. For example, the preferred substrate S' may be provided as a porous plate member that may be formed by powder metallurgy using, e.g., alumina or stainless steel. The substrate S may be prepared using a non-porous composition so as to incorporate the requisite array of vias by laser drilling or ablation, chemical etching, green tape cofire, or photo-ceramic processes. Preferably, the substrate S, S' is provided in a generally wafer-like profile having sufficient rigidity so as to be edge-mounted within a supporting means. The diffusion rate of hydrogen may be increased by heating the substrate S, S' so as to elevate the temperature of the palladium deposits D. The necessary heat may be applied to the deposits by integration of suitable heating means with the planar palladium structure. One contemplated heating means includes the use of a substrate material that permits resistive or inductive heating of the substrate to occur upon the application of electric current across the planar palladium structure.

Accordingly, it is contemplated that the requisite heating is controlled in some fashion so as to selectively control or enhance the diffusion rate. Such means offers an additional advantage: the presence of hydrogen in the planar palladium structure causes a change in the resistivity of the planar palladium structure, and therefore the diffusion rate may be sensed and controlled by a control system.

Another contemplated heating means would include the integration by bonding, etc. of a spiral, thin-film resistive element onto one major surface of the planar palladium structure. Still another heating means may include a thermoelectric device such as a Peltier-effect heater attached to the periphery of the planar palladium structure.

In still another embodiment, the substrate S and the palladium deposits D may be constructed to exhibit an intrinsic, predetermined tensile stress so as to relieve the naturally-occurring expansion force that may develop in the palladium deposits D at high concentrations of dissolved hydrogen. One method of creating such an opposing tensile stress may be provided by creating a difference in the thermal expansion coefficients of the substrate S and the deposits D. For example, the substrate S may be chosen from those materials that exhibit a low coefficient of thermal expansion; a palladium alloy may then be deposited on the substrate after it has been heated to an elevated temperature; and an opposing tensile stress will be developed in the thin-film deposits as the substrate cools.

Figure 4:
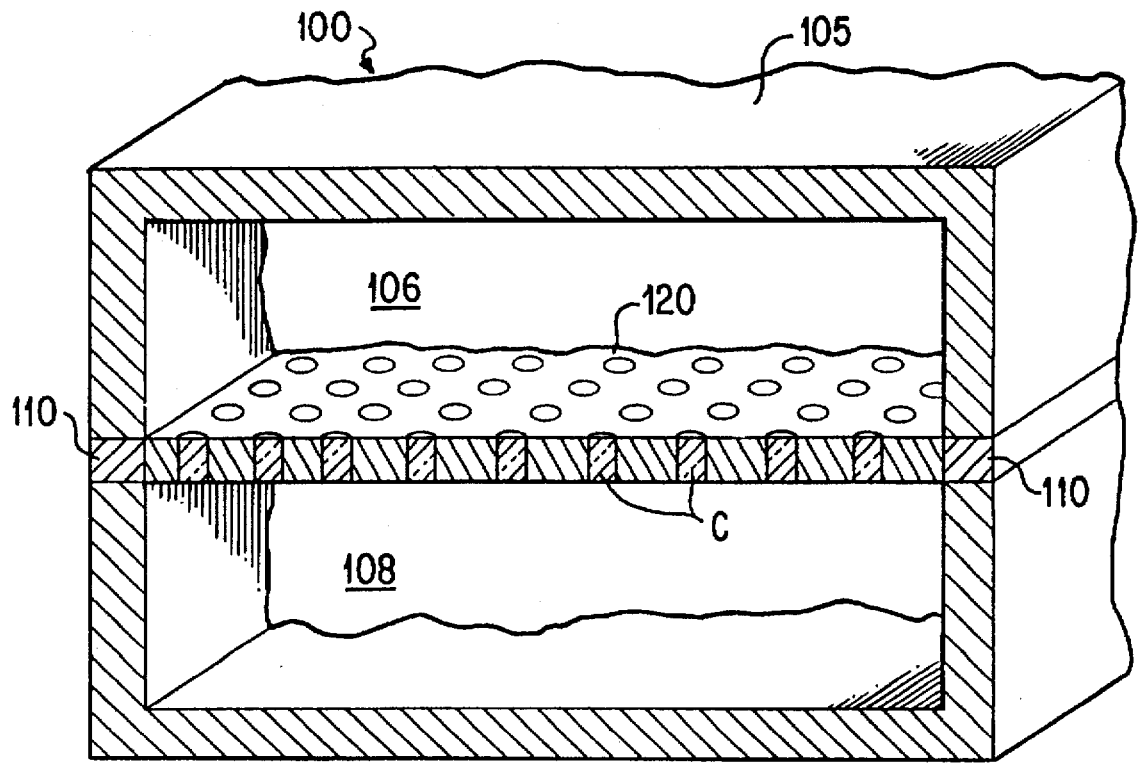
FIG. 4 is a side sectional view of a system for operating the planar palladium structure of FIG. 1 for providing a controlled concentration of hydrogen in a closed cavity.

The teachings of the present invention may also be applied to use in applications that may benefit from the provision of a controlled cavity pressure, such as a vacuum or a near-vacuum, in a closed cavity. Accordingly, and as illustrated in FIG. 4, another aspect of the present invention is directed to apparatus and methods to effect a selected concentration of hydrogen within one or more cavity volumes of a cavity system.

The illustrated system 100 includes a housing 105 that defines a cavity within which is located a hydrogen-permeable membrane 120 constructed according to the present invention. For the purposes of this description, the cavity will be considered as being enclosed by the housing 105; the cavity may be considered to be self-contained or to allow a flow therethrough of hydrogen or other gasses at selectable flow rates and concentrations; the volume defined therein will be considered to be separated by the membrane 120 into an upper cavity volume 106 and a lower cavity volume 108; and the pressure of the upper cavity volume 106 and lower cavity volume 108 (which will be seen to be selectable) will be identified respectively as the upper cavity pressure and lower cavity pressure. The cavity is contemplated as being accessible from outside of the housing 105, with provision of known gas supply and venting means (not shown), but nonetheless subject to pressurization by use of gas-tight edge mounting means 110 so as to locate the membrane 120 to provide a gas-tight, but hydrogen-permeable barrier between the upper cavity volume 106 or lower cavity volume 108. For example, in some embodiments, a check valve (not shown) may be provided for venting or purging gases from the upper cavity volume 106 and/or lower cavity volume 108.

It is contemplated that the membrane 120 may be employed according to the teachings herein to control the transfer of hydrogen between the upper cavity volume 106 and lower cavity volume 108. Selective operation of the membrane 120 can therefore provide an exchange of hydrogen between the upper cavity volume 106 and lower cavity volume 108. Alternatively, a vacuum or near vacuum may be created in the upper cavity volume 106 by filling the upper cavity volume 106 with pure hydrogen, followed by the provision of a hydrogen-free gas mixture in the lower cavity volume 108. Diffusion of hydrogen from the upper cavity volume 106 to the lower cavity volume 108 thereby creates a vacuum or near-vacuum in the upper cavity volume 106.

The mounting means 110 may include suitable thermally- and electrically-insulating connectors (not shown) so as to provide electrical current to the membrane 120 for causing resistive or inductive heating therein, or for providing electric current to a heating means operable by, e.g., resistive, inductive, or thermoelectric heating process, which may be integrated within the membrane 120.

In an alternative mode of operation, the system 100 may be constructed in an evacuated environment such that the lower cavity volume 108 is initially at a vacuum. Alternatively, any gases present in the lower cavity volume 108 may be purged and replaced by a predetermined concentration of hydrogen gas. A first gas mixture, preferably under pressure, fills the upper cavity volume 106 and purge any gases previously contained in the upper cavity volume. The partial pressure of hydrogen attains a sufficient concentration in the upper cavity volume 106 such that the hydrogen migrates through the palladium cells distributed throughout the membrane 120. The migration of hydrogen then displaces (purges) any gases that are present in the lower cavity volume 108 through suitable means such as a check valve. Any gases previously contained in the upper and lower cavity volumes 106, 108 are discarded, thus leaving only a selectable and equal partial pressure of hydrogen in both the upper and lower cavity volumes 106, 108. Thereafter, a desired concentration of hydrogen may be obtained in the cavity by altering the concentration of hydrogen in either of the upper cavity volume 106 or the lower cavity volume 108. For example, to increase the hydrogen concentration in the lower cavity volume, the flow of hydrogen into the upper cavity volume 106 is increased. The flow of hydrogen increases the concentration of hydrogen in the upper cavity volume 106, thus again disturbing the equilibrium and causing a migration of hydrogen gas from the upper cavity volume 106 to the lower cavity volume 108. Such a flow of hydrogen can be used to alter the concentration of hydrogen in the lower cavity volume 108 to acquire a new and desired pressure.

The presence of hydrogen at a sufficiently high concentration in the palladium deposits D in the planar palladium structures described herein would heretofore cause the palladium deposits D to experience the expansion and contraction described hereinabove with respect to the prior art. However, in a particular feature of the invention, the bulk of the substrate is believed to successfully constrain the stress and potential deformation of the palladium alloy deposits. Furthermore, by using microfine (i.e., very small diameter) channels C, the thickness of the palladium deposit can be minimized. As a result, the hydrogen pumping efficiency of the contemplated planar palladium structures is enhanced, and the contemplated planar palladium structures avoid the failure modes described hereinabove with respect to conventional palladium structures.

The illustrated planar palladium structures are thus expected to exhibit greater reliability and a longer operating life than is offered in conventional palladium structures. Further, the density, size, and thickness of the palladium alloy deposits can be selected at manufacturing to achieve an optimal diffusion rate of hydrogen.

What is claimed is:

1. A planar palladium structure, comprising:
    a planar substrate having upper and lower major surfaces and an array of channels extending therebetween, said channels allowing gaseous communication between said upper and lower major surfaces; and
    an array of plural, discrete palladium deposits being distributed on the substrate, said deposits being located in respective channels, said array being distributed with respect to said channels so as to restrict said gaseous communication between said upper and lower major surfaces to a diffusion of hydrogen gas through said deposits;
    whereby the substrate constrains the deformation of the palladium deposits due to the diffused hydrogen gas.

2. The structure of claim 1, wherein each of the palladium deposits comprises a thin film layer having an average thickness in the range of 0.1 micrometers to 1 millimeter.

3. The structure of claim 1, wherein each of the palladium deposits comprises a discrete thin film layer located within the respective one of said channels.

4. The structure of claim 1, wherein each of the palladium deposits comprises a discrete thin film layer located over an end of the respective one of said channels.

5. The structure of claim 1, wherein the substrate further comprises a composition of material capable of resisting the flow of electric current therethrough so as to exhibit a temperature increase by way of resistive heating.

6. The structure of claim 1, wherein the substrate further comprises an integral heating element.

7. The structure of claim 1, wherein the channels are regularly spaced.

8. The structure of claim 1, wherein said channels are irregularly spaced.

9. The structure of claim 1, wherein the substrate is formed of porous material.

10. A hydrogen pump system comprising:

a housing that defines a closed cavity;

a planar palladium structure attached within the closed cavity so as to provide upper and lower subcavities, said planar palladium structure including a planar substrate having upper and lower major surfaces and an array of hollow channels extending therebetween, said channels allowing gaseous communication between said upper and lower major surfaces, and an array of plural, discrete palladium deposits being distributed on the substrate, said deposits being located in a respective channels, said array being distributed with respect to said channels so as to restrict said gaseous communication between said upper and lower major surfaces to diffusion of hydrogen gas through said deposits;

whereby the substrate constrains the deformation of the palladium deposits due to the diffused hydrogen gas; and a system for providing hydrogen in at least one of the upper and lower subcavities.

11. The hydrogen pump system of claim 10, further comprising means for heating or cooling the planar palladium structure.

* * * * *